(12) United States Patent
Chung et al.

(10) Patent No.: US 12,292,443 B2
(45) Date of Patent: May 6, 2025

(54) CIRCULATING TUMOR CELL BASED BIOMARKER COMPOSITION FOR DIAGNOSIS AND PROGNOSIS OF METASTATIC PROSTATE CANCER

(71) Applicants: INJE UNIVERSITY INDUSTRY-ACADEMIC COOPERATION FOUNDATION, Gimhae-si (KR); SEOUL NATIONAL UNIVERSITY HOSPITAL, Seoul (KR)

(72) Inventors: Jae Seung Chung, Busan (KR); Ki-Ho Han, Busan (KR); Hyung Seok Cho, Busan (KR); Jae Il Chung, Busan (KR); Seok-Soo Byun, Seongnam-si (KR)

(73) Assignees: INJE UNIVERSITY INDUSTRY-ACADEMIC COOPERATION FOUNDATION, Gimhae-si (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 790 days.

(21) Appl. No.: 17/608,992

(22) PCT Filed: Apr. 28, 2021

(86) PCT No.: PCT/KR2021/005355
§ 371 (c)(1),
(2) Date: Nov. 5, 2021

(87) PCT Pub. No.: WO2021/221452
PCT Pub. Date: Nov. 4, 2021

(65) Prior Publication Data
US 2022/0214346 A1  Jul. 7, 2022

(30) Foreign Application Priority Data

Apr. 29, 2020 (KR) .................. 10-2020-0052737

(51) Int. Cl.
| | | |
|---|---|---|
| G01N 33/574 | (2006.01) | |
| A61K 31/337 | (2006.01) | |
| A61P 35/00 | (2006.01) | |
| C12Q 1/00 | (2006.01) | |
| C12Q 1/68 | (2018.01) | |
| C12Q 1/6886 | (2018.01) | |
| G01N 33/00 | (2006.01) | |
| G01N 33/50 | (2006.01) | |
| G01N 33/543 | (2006.01) | |

(52) U.S. Cl.
CPC . *G01N 33/57492* (2013.01); *G01N 33/57434* (2013.01); *A61K 31/337* (2013.01); *A61P 35/00* (2018.01); *C12Q 1/6886* (2013.01); *C12Q 2600/118* (2013.01); *C12Q 2600/158* (2013.01); *G01N 33/54326* (2013.01); *G01N 2333/4742* (2013.01); *G01N 2333/705* (2013.01); *G01N 2333/70596* (2013.01); *G01N 2333/723* (2013.01)

(58) Field of Classification Search
CPC ....... G01N 33/57492; G01N 33/57434; G01N 2333/705; G01N 2333/4742; G01N 2333/723; G01N 33/54326; C12Q 1/6886; C12Q 2600/118; C12Q 2600/158
See application file for complete search history.

(56) References Cited

U.S. PATENT DOCUMENTS

| | | | |
|---|---|---|---|
| 6,623,982 B1 * | 9/2003 | Liberti ............. | G01N 33/54326 436/805 |
| 9,952,221 B2 * | 4/2018 | Guyon ................ | C12Q 1/6886 |
| 2014/0235479 A1 | 8/2014 | Depinho et al. | |

FOREIGN PATENT DOCUMENTS

| | | | |
|---|---|---|---|
| JP | 2018-138042 A | 9/2018 | |
| KR | 10-2017-0131516 A | 11/2017 | |
| KR | 10-2020-0000969 A | 1/2020 | |
| WO | WO-2017062505 A1 * | 4/2017 | ........... A61K 31/337 |

OTHER PUBLICATIONS

Liu et al. Circulating tumor cells in prostate cancer: Precision diagnosis and therapy. Oncol Lett. Aug. 2017;14(2):1223-1232. doi: 10.3892/ol.2017.6332. Epub Jun. 7, 2017. PMID: 28789337; PMCID: PMC5529747. (Year: 2017).*

International Search Report for PCT/KR2021/005355 mailed Aug. 10, 2021 from Korean Intellectual Property Office.

(Continued)

*Primary Examiner* — Maher M Haddad
*Assistant Examiner* — Alec Jon Peters
(74) *Attorney, Agent, or Firm* — Revolution IP, PLLC

(57) ABSTRACT

The present invention relates to a biomarker composition for diagnosing and predicting prognosis of prostate cancer, and that the detection rate and expression level of gene combination composed with AR (Androgen receptor), AR-V7 (Androgen receptor variant 7), EpCAM (Epithelial cell adhesion molecule) in blood tumor cells (CTC) isolated from patients, Epithelial cell adhesion molecule), KRT-19 (Cytokeratin 19), PSA (Prostate specific antigen), and PSMA (Prostate specific membrane antigen) in circulating tumor cells (CTCs) isolated from patients is related to the level of malignancy in prostate cancer is confirmed and thus the gene combination provides as a biomarker for prostate cancer diagnosis and a biomarker for prognosis prediction of prostate cancer.

3 Claims, 8 Drawing Sheets
Specification includes a Sequence Listing.

(56) References Cited

OTHER PUBLICATIONS

Josefsson, Andreas et al., "Gene Expression Alterations during Development of Castration-Resistant Prostate Cancer Are Detected in Circulating Tumor Cells", Cancers, Dec. 21, 2019, vol. 12, No. 39, pp. 1-13.
Josefsson, Andreas et al., "Circulating tumor cells mirror bone metastatic phenotype in prostate cancer", Oncotarget, 2018, vol. 9, No. 50, pp. 29403-29413.
Bastos, Diogo A. et al., "CTC-derived AR-V7 detection as a prognostic and predictive biomarker in advanced prostate cancer", Expert Review of Molecular Diagnostics, 2018, DOI: 10.1080/14737159.2018.1427068.

* cited by examiner

[FIG. 1]
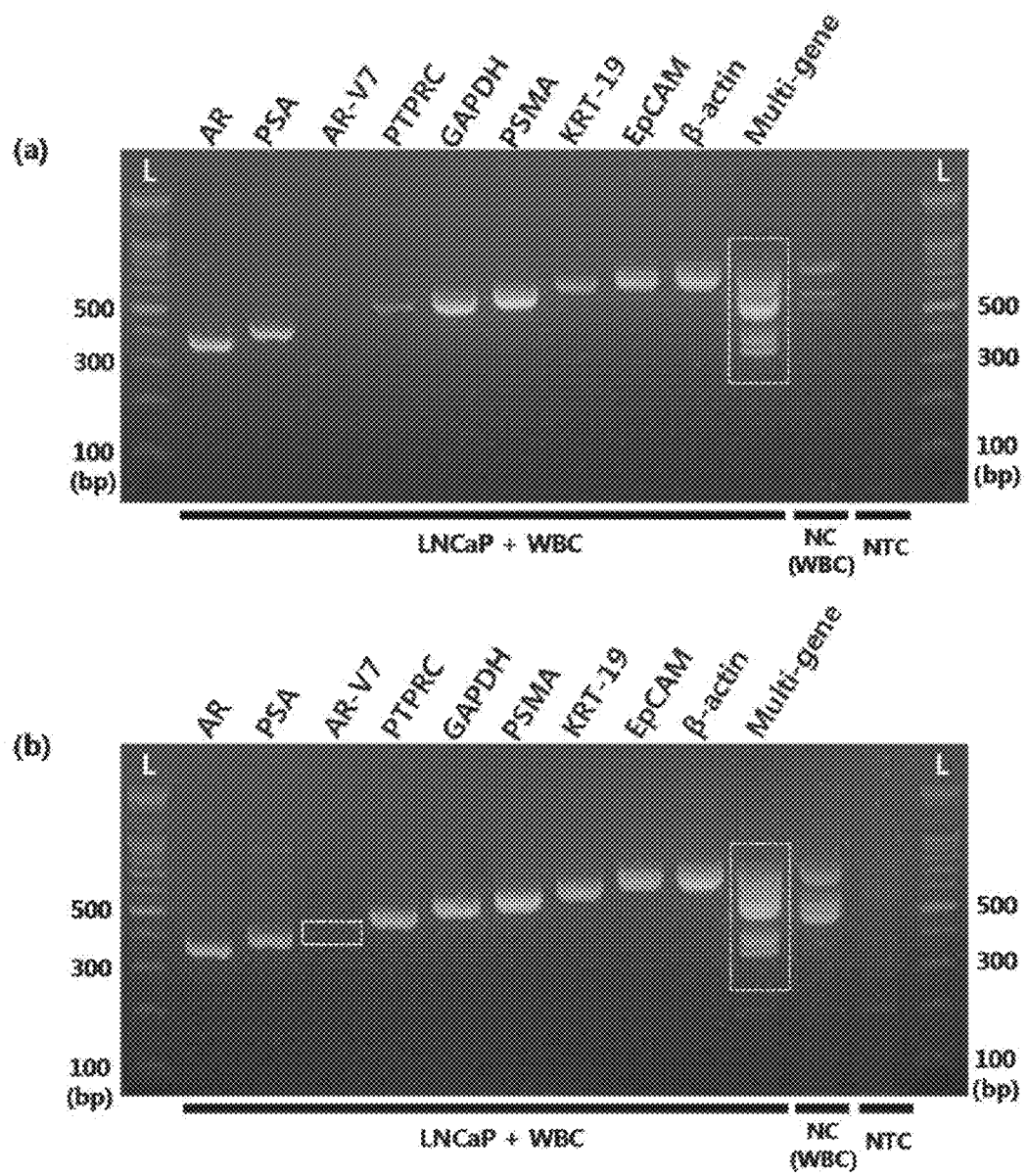

[FIG. 2]
(a)
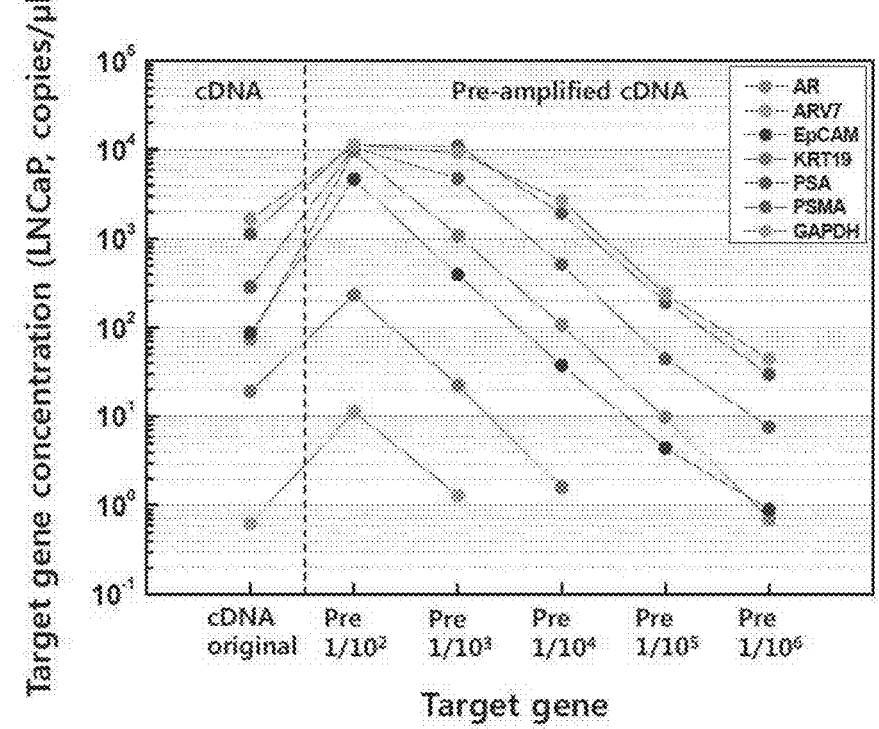
(b)
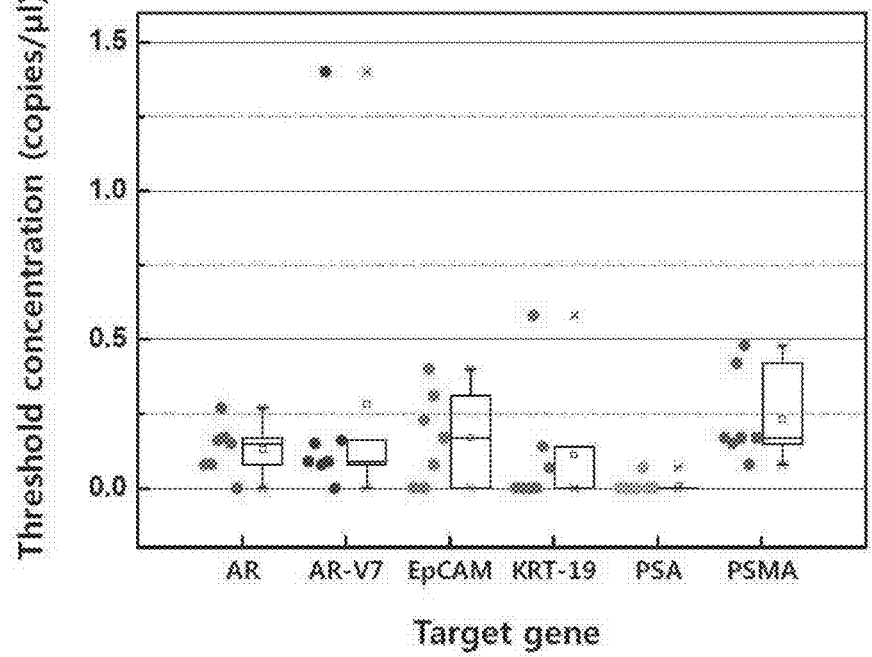

[FIG. 3]
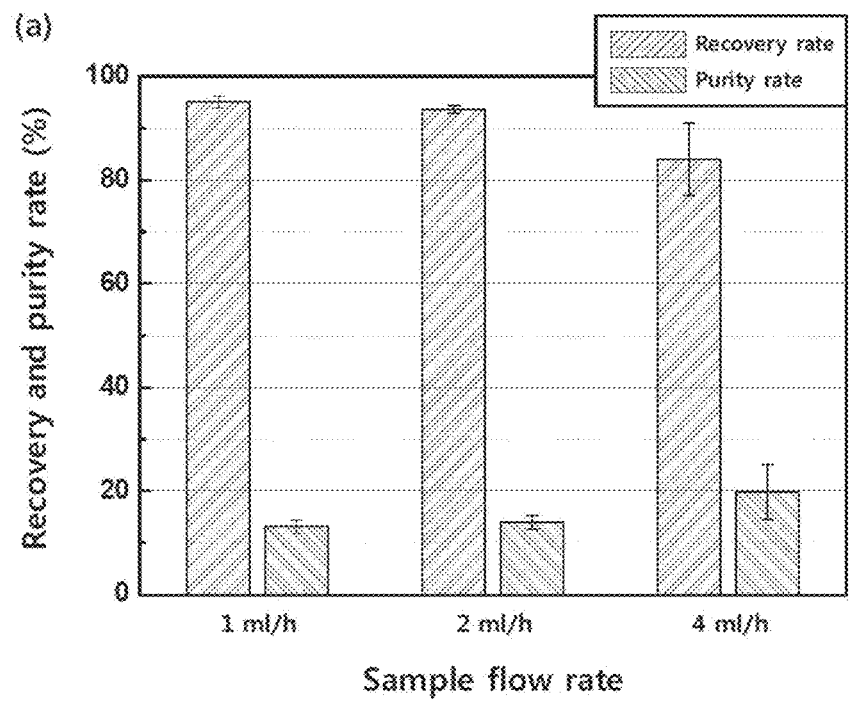
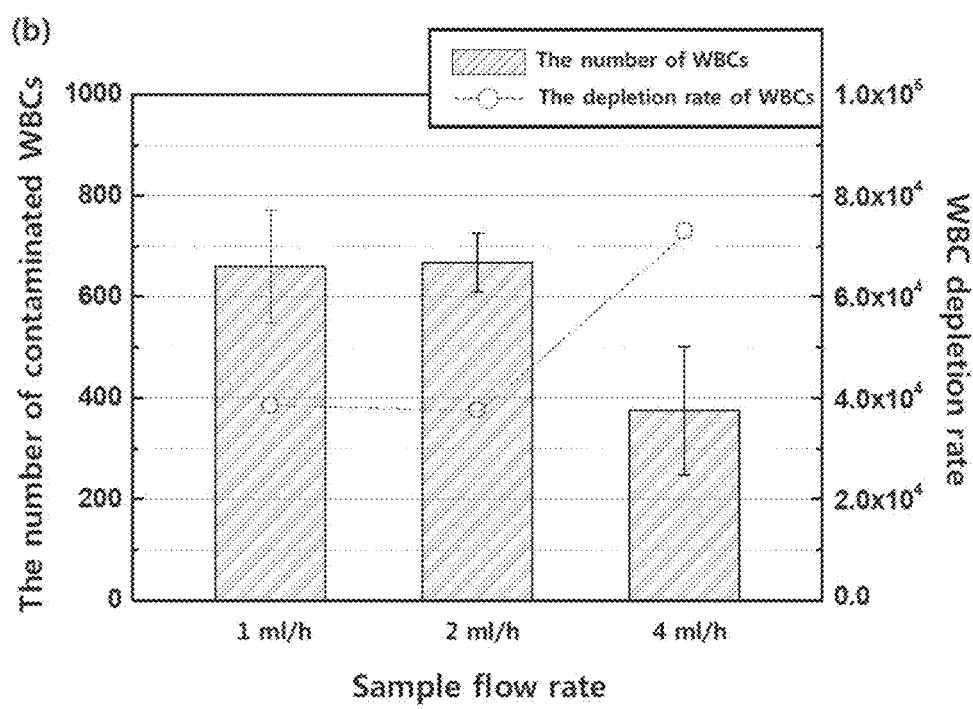

[FIG. 4]
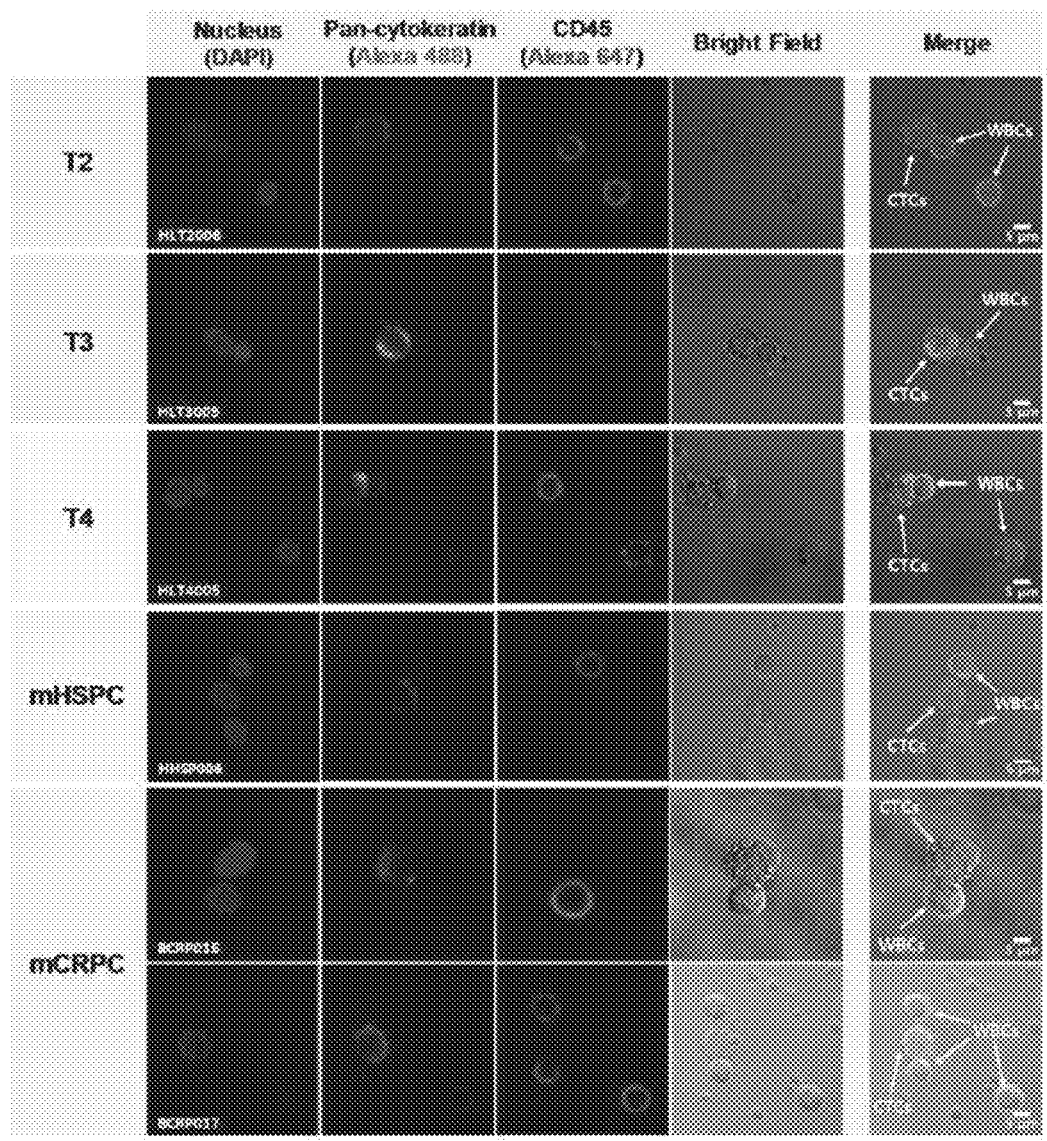

[FIG. 5]
(a)
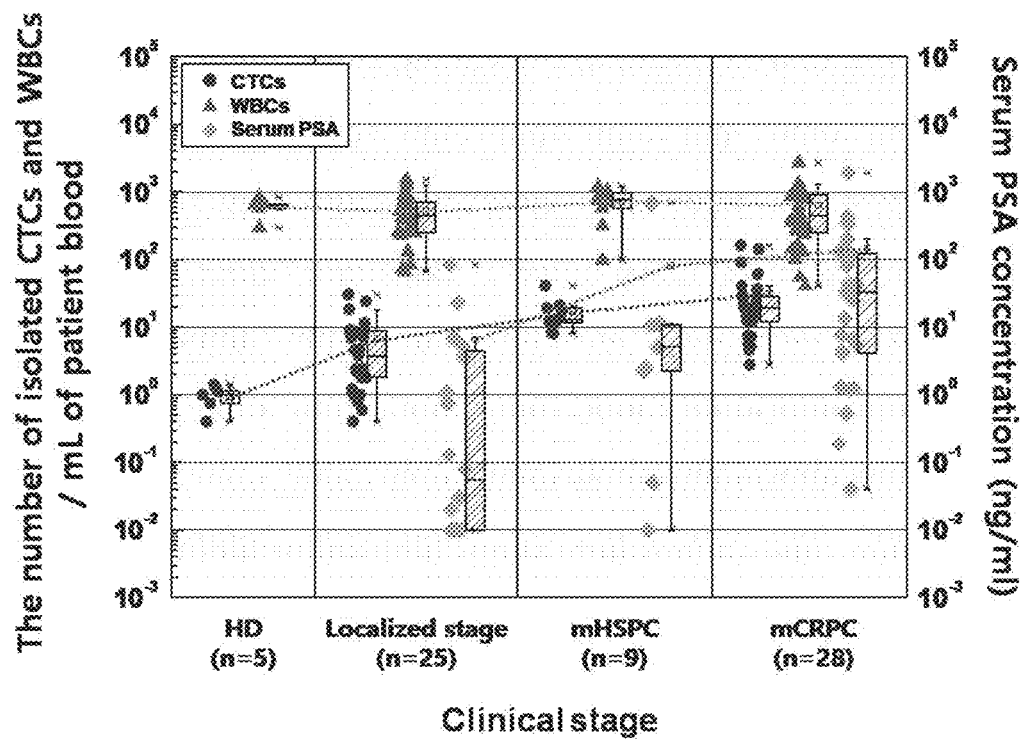
(b)
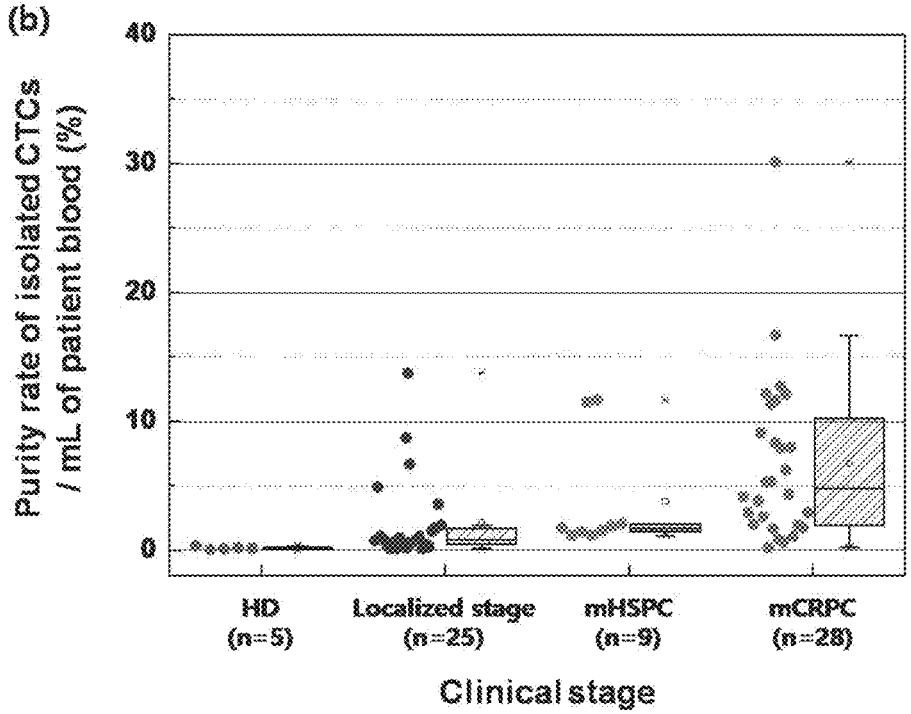

[FIG. 6]
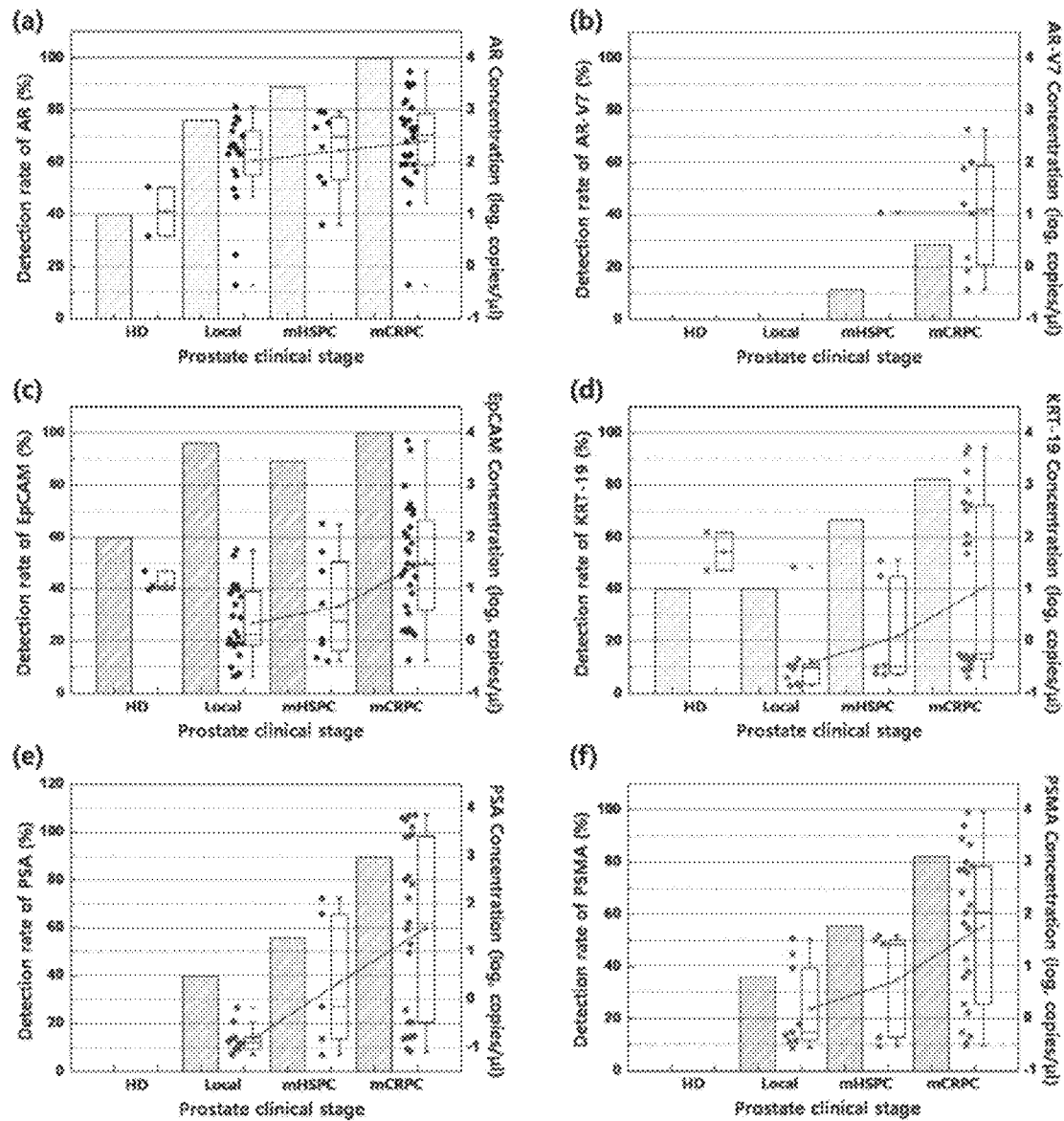

[FIG. 7]
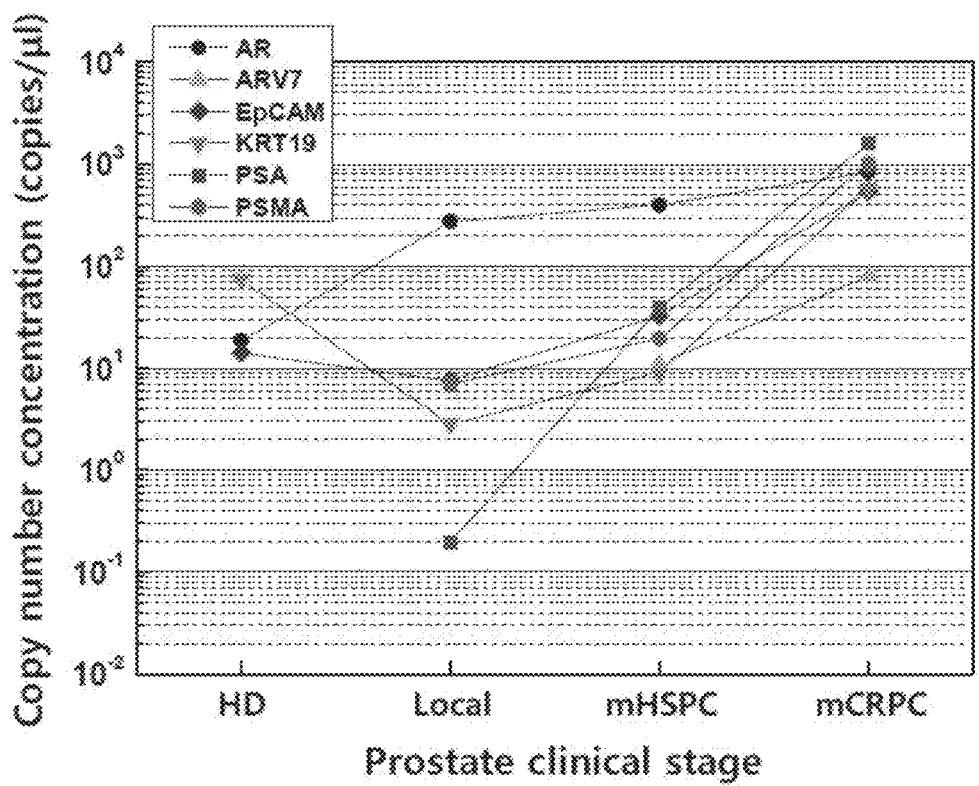

[FIG. 8]
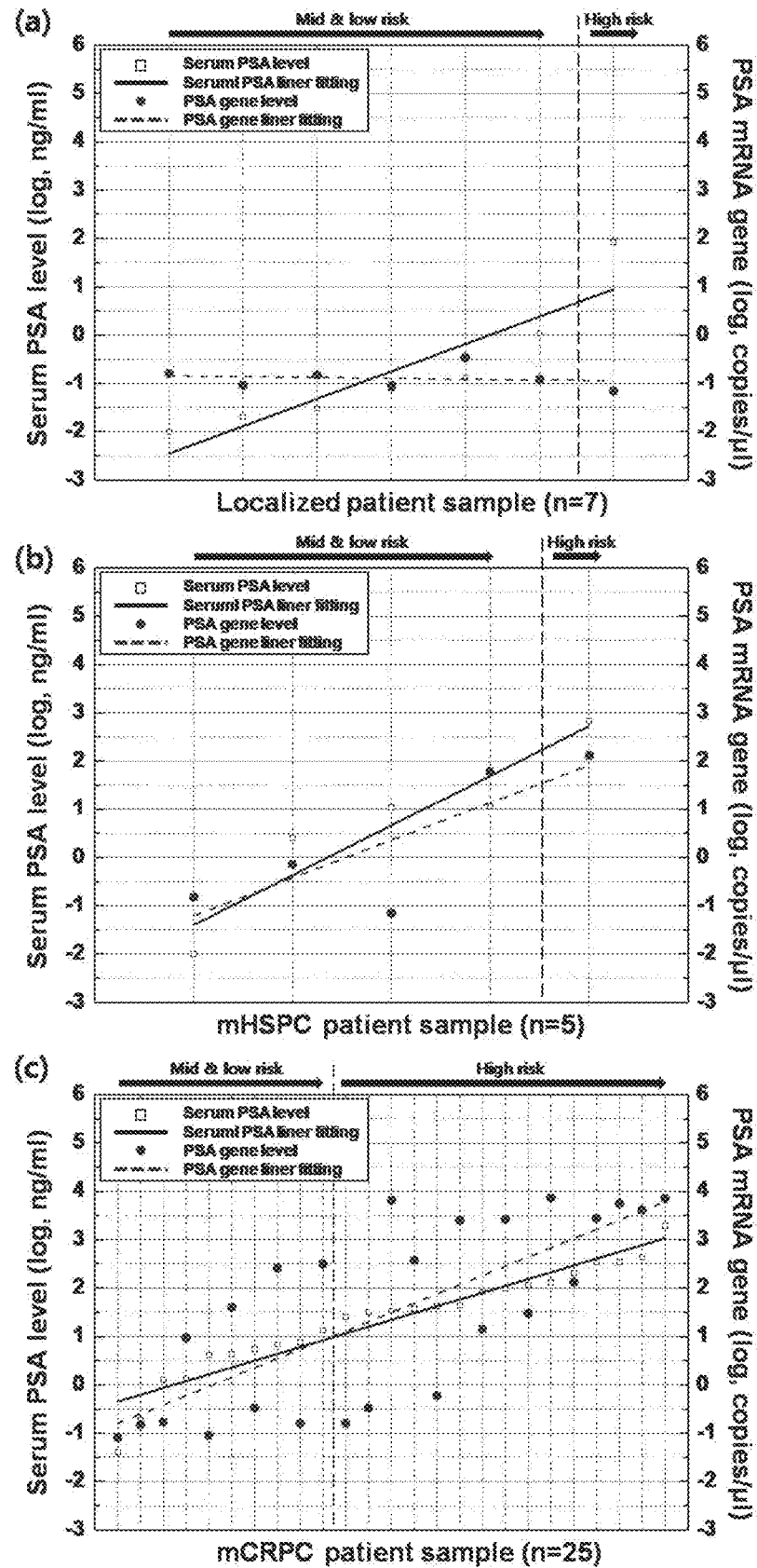

```
                           SEQUENCE LISTING

<160> NUMBER OF SEQ ID NOS: 36

<210> SEQ ID NO 1
<211> LENGTH: 21
<212> TYPE: DNA
<213> ORGANISM: Artificial Sequence
<220> FEATURE:
<223> OTHER INFORMATION: pre-ar-f

<400> SEQUENCE: 1
tctctcaaga gtttggatgg c                                             21

<210> SEQ ID NO 2
<211> LENGTH: 21
<212> TYPE: DNA
<213> ORGANISM: Artificial Sequence
<220> FEATURE:
<223> OTHER INFORMATION: pre-ar-r

<400> SEQUENCE: 2
actgggtgtg gaaatagatg g                                             21

<210> SEQ ID NO 3
<211> LENGTH: 18
<212> TYPE: DNA
<213> ORGANISM: Artificial Sequence
<220> FEATURE:
<223> OTHER INFORMATION: pre-arv7-f

<400> SEQUENCE: 3
gtgcgccagc agaaatga                                                 18

<210> SEQ ID NO 4
<211> LENGTH: 20
<212> TYPE: DNA
<213> ORGANISM: Artificial Sequence
<220> FEATURE:
<223> OTHER INFORMATION: pre-arv7-r

<400> SEQUENCE: 4
atgccaagcc acattacagg                                               20

<210> SEQ ID NO 5
<211> LENGTH: 16
<212> TYPE: DNA
<213> ORGANISM: Artificial Sequence
<220> FEATURE:
<223> OTHER INFORMATION: pre-epcam-f

<400> SEQUENCE: 5
ctcgcgttcg ggcttc                                                   16
```

<210> SEQ ID NO 6
<211> LENGTH: 24
<212> TYPE: DNA
<213> ORGANISM: Artificial Sequence
<220> FEATURE:
<223> OTHER INFORMATION: pre-epcam-r

<400> SEQUENCE: 6
tcaggtgctt tttcatcaac ataa                                              24

<210> SEQ ID NO 7
<211> LENGTH: 21
<212> TYPE: DNA
<213> ORGANISM: Artificial Sequence
<220> FEATURE:
<223> OTHER INFORMATION: pre-krt19-f

<400> SEQUENCE: 7
cgactacagc cactactaca c                                                 21

<210> SEQ ID NO 8
<211> LENGTH: 20
<212> TYPE: DNA
<213> ORGANISM: Artificial Sequence
<220> FEATURE:
<223> OTHER INFORMATION: pre-krt19-r

<400> SEQUENCE: 8
cactatcagc tcgcacatcg                                                   20

<210> SEQ ID NO 9
<211> LENGTH: 18
<212> TYPE: DNA
<213> ORGANISM: Artificial Sequence
<220> FEATURE:
<223> OTHER INFORMATION: pre-psa-f

<400> SEQUENCE: 9
ggtgatgact ccagccac                                                     18

<210> SEQ ID NO 10
<211> LENGTH: 20
<212> TYPE: DNA
<213> ORGANISM: Artificial Sequence
<220> FEATURE:
<223> OTHER INFORMATION: pre-psa-r

<400> SEQUENCE: 10
cacgatggtg tccttgatcc                                                   20

<210> SEQ ID NO 11
<211> LENGTH: 24
<212> TYPE: DNA
<213> ORGANISM: Artificial Sequence
<220> FEATURE:
<223> OTHER INFORMATION: pre-psma-f

<400> SEQUENCE: 11
agcatttttg gatgaattga aagc                                              24

<210> SEQ ID NO 12
<211> LENGTH: 19
<212> TYPE: DNA
<213> ORGANISM: Artificial Sequence
<220> FEATURE:

<223> OTHER INFORMATION: pre-psma-r

<400> SEQUENCE: 12
tgggtaacct ggtgtgaga                                                    19

<210> SEQ ID NO 13
<211> LENGTH: 15
<212> TYPE: DNA
<213> ORGANISM: Artificial Sequence
<220> FEATURE:
<223> OTHER INFORMATION: pre-bactin-f

<400> SEQUENCE: 13
ggcaccaggg cgtga                                                        15

<210> SEQ ID NO 14
<211> LENGTH: 15
<212> TYPE: DNA
<213> ORGANISM: Artificial Sequence
<220> FEATURE:
<223> OTHER INFORMATION: pre-bactin-r

<400> SEQUENCE: 14
gccgccagac agcac                                                        15

<210> SEQ ID NO 15
<211> LENGTH: 20
<212> TYPE: DNA
<213> ORGANISM: Artificial Sequence
<220> FEATURE:
<223> OTHER INFORMATION: pre-gapdh-f

<400> SEQUENCE: 15
agaacgggaa gcttgtcatc                                                   20

<210> SEQ ID NO 16
<211> LENGTH: 20
<212> TYPE: DNA
<213> ORGANISM: Artificial Sequence
<220> FEATURE:
<223> OTHER INFORMATION: pre-gapdh-r

<400> SEQUENCE: 16
ctgcttcacc accttcttga                                                   20

<210> SEQ ID NO 17
<211> LENGTH: 22
<212> TYPE: DNA
<213> ORGANISM: Artificial Sequence
<220> FEATURE:
<223> OTHER INFORMATION: pre-ptprc-f

<400> SEQUENCE: 17
tgttgtaaag atcaaccagc ac                                                22

<210> SEQ ID NO 18
<211> LENGTH: 19
<212> TYPE: DNA
<213> ORGANISM: Artificial Sequence
<220> FEATURE:
<223> OTHER INFORMATION: pre-ptprc-r

<400> SEQUENCE: 18
ctgtgtcctc cagctccta                                                    19

```
<210> SEQ ID NO 19
<211> LENGTH: 21
<212> TYPE: DNA
<213> ORGANISM: Artificial Sequence
<220> FEATURE:
<223> OTHER INFORMATION: ar-f

<400> SEQUENCE: 19
cagcctattg cgagagagct g                                          21

<210> SEQ ID NO 20
<211> LENGTH: 21
<212> TYPE: DNA
<213> ORGANISM: Artificial Sequence
<220> FEATURE:
<223> OTHER INFORMATION: ar-r

<400> SEQUENCE: 20
gaaaggatct tgggcacttg c                                          21

<210> SEQ ID NO 21
<211> LENGTH: 26
<212> TYPE: DNA
<213> ORGANISM: Artificial Sequence
<220> FEATURE:
<223> OTHER INFORMATION: arv7-f

<400> SEQUENCE: 21
ccatcttgtc gtcttcggaa atgtta                                     26

<210> SEQ ID NO 22
<211> LENGTH: 26
<212> TYPE: DNA
<213> ORGANISM: Artificial Sequence
<220> FEATURE:
<223> OTHER INFORMATION: arv7-r

<400> SEQUENCE: 22
tttgaatgag gcaagtcagc ctttct                                     26

<210> SEQ ID NO 23
<211> LENGTH: 18
<212> TYPE: DNA
<213> ORGANISM: Artificial Sequence
<220> FEATURE:
<223> OTHER INFORMATION: epcam-f

<400> SEQUENCE: 23
gttcgggctt ctgcttgc                                              18

<210> SEQ ID NO 24
<211> LENGTH: 19
<212> TYPE: DNA
<213> ORGANISM: Artificial Sequence
<220> FEATURE:
<223> OTHER INFORMATION: epcam-r

<400> SEQUENCE: 24
gctctcatcg cagtcagga                                             19

<210> SEQ ID NO 25
<211> LENGTH: 20
<212> TYPE: DNA
<213> ORGANISM: Artificial Sequence
<220> FEATURE:
<223> OTHER INFORMATION: krt19-f
```

```
<400> SEQUENCE: 25
tttgagacgg aacaggctct                                          20

<210> SEQ ID NO 26
<211> LENGTH: 20
<212> TYPE: DNA
<213> ORGANISM: Artificial Sequence
<220> FEATURE:
<223> OTHER INFORMATION: krt19-r

<400> SEQUENCE: 26
aatccacctc cacactgacc                                          20

<210> SEQ ID NO 27
<211> LENGTH: 24
<212> TYPE: DNA
<213> ORGANISM: Artificial Sequence
<220> FEATURE:
<223> OTHER INFORMATION: psa-f

<400> SEQUENCE: 27
accagaggag ttcttgaccc caaa                                     24

<210> SEQ ID NO 28
<211> LENGTH: 20
<212> TYPE: DNA
<213> ORGANISM: Artificial Sequence
<220> FEATURE:
<223> OTHER INFORMATION: psa-r

<400> SEQUENCE: 28
ccccagaatc acccgagcag                                          20

<210> SEQ ID NO 29
<211> LENGTH: 27
<212> TYPE: DNA
<213> ORGANISM: Artificial Sequence
<220> FEATURE:
<223> OTHER INFORMATION: psma-f

<400> SEQUENCE: 29
atgaattgaa agctgagaac atcaaga                                  27

<210> SEQ ID NO 30
<211> LENGTH: 25
<212> TYPE: DNA
<213> ORGANISM: Artificial Sequence
<220> FEATURE:
<223> OTHER INFORMATION: psma-r

<400> SEQUENCE: 30
gggatgagtc ttatttgggt aggac                                    25

<210> SEQ ID NO 31
<211> LENGTH: 22
<212> TYPE: DNA
<213> ORGANISM: Artificial Sequence
<220> FEATURE:
<223> OTHER INFORMATION: bactin-f

<400> SEQUENCE: 31
gtaccactgg catcgtgatg ga                                       22

<210> SEQ ID NO 32
<211> LENGTH: 23
```

```
<212> TYPE: DNA
<213> ORGANISM: Artificial Sequence
<220> FEATURE:
<223> OTHER INFORMATION: bactin-r

<400> SEQUENCE: 32
gccatctctt gctcgaagtc cag                                                  23

<210> SEQ ID NO 33
<211> LENGTH: 20
<212> TYPE: DNA
<213> ORGANISM: Artificial Sequence
<220> FEATURE:
<223> OTHER INFORMATION: gapdh-f

<400> SEQUENCE: 33
tgcaccacca actgcttagc                                                      20

<210> SEQ ID NO 34
<211> LENGTH: 21
<212> TYPE: DNA
<213> ORGANISM: Artificial Sequence
<220> FEATURE:
<223> OTHER INFORMATION: gapdh-r

<400> SEQUENCE: 34
ggcatggact gtggtcatga g                                                    21

<210> SEQ ID NO 35
<211> LENGTH: 22
<212> TYPE: DNA
<213> ORGANISM: Artificial Sequence
<220> FEATURE:
<223> OTHER INFORMATION: ptprc-f

<400> SEQUENCE: 35
cttcagtggt cccattgtgg tg                                                   22

<210> SEQ ID NO 36
<211> LENGTH: 22
<212> TYPE: DNA
<213> ORGANISM: Artificial Sequence
<220> FEATURE:
<223> OTHER INFORMATION: ptprc-r

<400> SEQUENCE: 36
ccactttgtt ctcggcttcc ag                                                   22
```

CIRCULATING TUMOR CELL BASED BIOMARKER COMPOSITION FOR DIAGNOSIS AND PROGNOSIS OF METASTATIC PROSTATE CANCER

CROSS REFERENCE TO PRIOR APPLICATIONS

This application is the 35 U.S.C. 371 national stage of International application PCT/KR2021/005355 filed on Apr. 28, 2021 which claims priority to Korean Patent Application No. 10-2020-0052737 filed on Apr. 29, 2020. The entire contents of each of the above-identified applications are hereby incorporated by reference.

SEQUENCE LISTING

This application contains a Sequence Listing submitted via EFS-Web and hereby incorporated by reference in its entirety. The Sequence Listing is named 2280-368_SE-QCRF.txt, created on Oct. 6, 2021, and 7,067 bytes in size.

TECHNICAL FIELD

The present invention relates to a biomarker composition for diagnosis and prognosis of prostate cancer.

BACKGROUND ART

Prostate cancer is a cancer that occurs in the prostate, and most of them grow slowly, but an aggressive prostate cancer has been reported in some patients. In aggressive prostate cancer, cancer cells may metastasize to other parts of the body, particularly bones and lymph nodes, from the prostate and symptoms such as pain and difficulty in urinating may develop. Prostate cancer has no symptoms and is rarely detected, and most patients die without medical care.

The way of managing prostate cancer is determined by the degree of malignancy that the cancer progresses. The degree of malignancy of cancer is largely divided into a localized stage in which cancer cells exist only in the area where the cancer has occurred, and a metastatic stage in which cancer cells have the potential to metastasize to other areas, and the metastatic stage is classified as hormone-sensitive prostate cancer and castration-resistant prostate cancer.

It was reported that prostate cancer has hormone-dependent characteristics, so in the case of patients in the early localized stage, the 10-year survival rate is about 70-85% of the patients and recurrence occurs in the form of metastases within 7-10 years in 10-40%, when treated with removal of testicular androgens by surgical castration and radiation therapy. Metastatic prostate cancer is treated with androgen deprivation therapy (ADT), which deprives androgens, a male hormone, to induce growth reduction and apoptosis of cancer cells. At this time, most patients initially have a high response rate of 80-90%, however, after an average of 18 to 24 months, some patients develop cancer cells that no longer respond to ADT, and patients die within 1 to 2 years. This is called castration-resistant prostate cancer.

Historically, prostate cancer is known to be a cancer that does not respond well to chemotherapy. In particular, since in castration-resistant prostate cancer, there is no longer testosterone intervention and any effect of drugs acting on testosterone receptors, and the cancer continues to progress, despite many efforts to use chemotherapy for prostate cancer treatment, it is not showing a clear effect accordingly. Therefore, in order to develop a better treatment strategy for castration-resistant prostate cancer, it is very necessary to study the mechanism at the molecular level.

In order to develop a biomarker capable of accurately diagnosing the degree of malignancy in prostate cancer patients in view of the above, the present inventors confirmed that the level of the gene combination composed of AR (Androgen receptor), AR-V7 (Androgen receptor variant 7, androgen receptor variant 7), EpCAM (Epithelial cell adhesion molecule), KRT-19 (Cytokeratin 19), PSA (Prostate specific antigen), and PSMA (Prostate specific membrane antigen) in circulating tumor cells (CTC) isolated from cancer patients, is related to the level of malignancy in prostate cancer, and completed the present invention.

DISCLOSURE

Technical Problem

The present invention relates to a biomarker composition for diagnosing and predicting prognosis of prostate cancer, and the gene combination is provided as a biomarker for prostate cancer diagnosis and a biomarker for prognosis prediction of prostate cancer by confirming that the detection rate and expression level of the gene combination composed of AR (Androgen receptor), AR-V7 (Androgen receptor variant 7, androgen receptor variant 7), EpCAM (Epithelial cell adhesion molecule), KRT-19 (Cytokeratin 19), PSA (Prostate specific antigen), and PSMA (Prostate specific membrane antigen) in circulating tumor cells (CTC) isolated from patients, is related to the level of malignancy in prostate cancer.

Technical Solution

The present invention provides a biomarker composition for diagnosing metastatic prostate cancer comprising a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

Also, the present invention provides a kit for diagnosing metastatic prostate cancer comprising an agent capable of detecting gene expression level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

In addition, the present invention provides a method of providing information for diagnosis of metastatic prostate cancer comprising: (a) separating a circulating tumor cell (CTC) isolated from a biological sample; (b) extracting mRNA from the separated circulating tumor cells (OTC); (c) measuring mRNA level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) by using the extracted mRNA as a template: and (d) classifying as prostate cancer when the mRNA level of the genes is increased compared to that of a normal person.

Furthermore, the present invention provides a biomarker composition for predicting prognosis of metastasis potential to prostate cancer comprising a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

In addition, the present invention provides a kit for predicting prognosis of metastasis potential to prostate cancer comprising an agent capable of detecting gene expression level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

In addition, the present invention provides a method of providing information for predicting prognosis of metastasis potential to prostate cancer comprising: (a) separating a circulating tumor cell (CTC) isolated from a biological sample; (b) extracting mRNA from the separated circulating tumor cells (OTC); (c) measuring mRNA level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) by using the extracted mRNA as a template: and (d) classifying as prostate cancer when the mRNA level of the genes is increased compared to that of a normal person.

In addition, the present invention provides a method of screening an agent for preventing or treating metastatic prostate cancer comprising: a first step of selecting a disease subject by measuring expression level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) in a biological sample isolated from tissue of the subject; and a second step of judging as a formulation for preventing or treating metastatic prostate cancer if the expression level of the gene combination after treatment with a test substance decreases compared to a disease subject not treated with the test substance.

Advantageous Effects

According to the present invention, by confirming that the detection rate and expression level of gene combination composed with AR (Androgen receptor), AR-V7 (Androgen receptor variant 7), EpCAM (Epithelial cell adhesion molecule), KRT-19 (Cytokeratin 19), PSA (Prostate specific antigen), and PSMA (Prostate specific membrane antigen) in circulating tumor cells (OTCs) isolated from patients is related to the level of malignancy in prostate cancer, the gene combination can be provided as a biomarker for prostate cancer diagnosis and a biomarker for prognosis prediction of prostate cancer.

DESCRIPTION OF DRAWINGS

FIG. 1 illustrates a photograph showing pre-amplification results for analyzing AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) genes. (a) is a 30 cycle PCR result, and (b) is a 45 cycle PCR result, GAPDH and β-actin are housekeeping genes, and PTPRC is a leukocyte (WBC) specific gene.

FIG. 2 shows a graph of the results of ddPCR for analyzing AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) genes at cell level. (a) is a graph confirming the target gene concentration of the LNCaP cell line for confirming the pre-amplification setup, and (b) is a graph showing the threshold concentration of the target gene.

FIG. 3 shows a graph analyzing (a) recovery rate and purity rate of a microfluidic device, and (b) co-separated leukocytes (WBC) and leukocyte depletion rates, when prostate cancer diagnosis and prognosis prediction method according to the present invention is applied to a patient model, FIG. 4 illustrates a confocal micrograph showing CTC cells and co-separated white blood cells (WBC) isolated from mCRPC patients from localized stage T2. Green indicates Pan-cytokeratin positive CTC, and red indicates anti-CD45 positive white blood cells (WBC).

FIG. 5 shows a graph of measuring number of circulating tumor cells (CTC) and white blood cells (WBC) isolated per mL of patient blood, PSA concentration in blood (ng/mL), purity rate of isolated CTC per mL of patient blood according to the clinical stage of the cancer. HD represents a healthy donor, Localized stage represents the localized stage of cancer, mHSPC represents the stage of metastatic hormone-sensitive prostate cancer, and mCRPC represents the stage of metastatic castration-resistant prostate cancer.

FIG. 6 shows a graph of measuring the detection rate (%) and concentration (copy/μl) of cancer-related genes in the isolated OTCs according to the clinical stage of the cancer. (a) AR (Androgen receptor), (b) AR-V7 (Androgen receptor variant 7), (c) EpCAM (Epithelial cell adhesion molecule), (d) KRT-19 (Cytokeratin 19), (e) PSA (Prostate specific antigen) and (f) PSMA (Prostate specific membrane antigen). HD represents healthy donor (n=5), localized stage represents the localized stage of cancer (n=25), mHSPC represents the stage of metastatic hormone-sensitive prostate cancer (n=9), and mCRPC represents the stage of metastatic castration-resistant prostate cancer (n=28).

FIG. 7 shows a graph of measuring the expression level (copy/concentration) of cancer-related genes in normal donors and prostate cancer patients. HD represents a normal donor, Localized stage represents a localized stage of cancer, mHSPC represents the stage of metastatic hormone-sensitive prostate cancer, mCRPC represents the stage of metastatic castration-resistant prostate cancer stage. The expression levels of AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) genes were measured.

FIG. 8 is a graph of measuring blood PSA levels (ng/μl) and mRNA concentration (copy/μl) according to the clinical stage of cancer. (a) Localized stage represents the localized stage of cancer (n=7, serum PSA ($R2=0.79$ and $p=0.91$), PSA gene ($R2=-0.17$ and $\rho=-0.16$), (b) mHSPC represents the stage of metastatic hormone-sensitive prostate (n=5, serum PSA ($R2=0.83$ and $\rho=0.93$), PSA gene ($R2=0.56$ and $\rho=0.82$), and (c) mCRPC represents the stage of metastatic hormone-resistant prostate cancer (n=25, serum PSA ($R2=0.91$ and $\rho=0.96$), PSA gene ($R2=0.53$ and $\rho=0.74$)).

BEST MODE

Terms used in the present specification have selected general terms that are currently widely used as possible while taking functions of the present invention into consideration, but this may vary according to the intention or precedent of a technician working in this field, the emergence of new technologies, and the like. In addition, in certain cases, there are terms arbitrarily selected by the applicant, and in this case, the meaning of the terms will be described in detail in the description of the corresponding invention. Therefore, the terms used in the present invention should be defined based on the meaning of the term and the overall contents of the present invention, not a simple name of the term.

Unless otherwise defined, all terms used herein including technical or scientific terms have the same meaning as commonly understood by one of ordinary skill in the art to which the present invention belongs. Terms such as those defined in a commonly used dictionary should be interpreted as having a meaning consistent with the meaning in the context of the related technology, and should not be interpreted as an ideal or excessively formal meaning unless explicitly defined in this application.

The numerical range includes the numerical values defined in the above range. All maximum numerical limits given throughout this specification include all lower numerical limits as if the lower numerical limits were expressly written. All minimum numerical limits given throughout this specification include all higher numerical limits as if the higher numerical limits were expressly written. All numerical limits given throughout this specification will include all better numerical ranges within the wider numerical range, as if the narrower numerical limits were expressly written.

Hereinafter, the present invention will be described in more detail.

The present invention provides a biomarker composition for diagnosing metastatic prostate cancer comprising a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

The metastatic prostate cancer may be metastatic castration-resistant prostate cancer or metastatic hormone-sensitive prostate cancer, and the hormone-sensitive prostate cancer is hormone-sensitive prostate cancer in stages I to IV, hormone-sensitive recurrent prostate cancer, or hormone-sensitive metastatic prostate cancer. In the case of metastatic prostate cancer, testosterone blockade therapy is performed as a temporizing method, and most patients respond with a decrease in PSA, but eventually the apoptosis process is lost within 2 years and it progresses to castration-resistant prostate cancer that does not respond to male hormone blockade therapy. Castration-resistant prostate cancer refers to the stage of biochemical or clinical progression of prostate cancer, although blood testosterone is reduced to castration levels. Biochemical recurrence with an increase in PSA precedes clinical progression such as bone metastasis by several months and in general, it is known that it takes an average of 12 to 18 months from diagnosis of metastatic hormone refractory prostate cancer to death.

In addition, the present invention provides a kit for diagnosing metastatic prostate cancer comprising an agent capable of detecting gene expression level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

The agent capable of measuring the expression level of the gene may be a primer or probe that specifically binds to the gene, but it is not limited thereto.

The 'gene expression level' can be measured using an antisense oligonucleotide, a primer pair or a probe that specifically binds to the mRNA of a gene, and the agent for measuring the expression of the mRNA is selected from the group consisting of an antisense oligonucleotide, a primer pair, a probe and a combination thereof, which are specific for the gene. That is, the detection of a nucleic acid may be performed by an amplification reaction using one or more oligonucleotide primers to be hybridized to a nucleic acid molecule encoding a gene or a complement of the nucleic acid molecule, but it is not limited thereto. For example, detection of mRNA using primers can be performed by amplifying the gene sequence using an amplification method such as PCR, and then confirming whether amplification is performed by a method known in the art, and it can be measured by RT-PCR, competitive RT-PCR, quantitative RT-PCR, RNase protection assay, Northern blot or DNA chip, but it is not limited thereto.

The "probe" refers to a nucleic acid fragment such as RNA or DNA corresponding to a short number of bases to several hundred bases capable of specifically binding to an mRNA, and it is labeled so that the presence or absence of specific mRNA and the amount of expression can be confirmed. The probe may be manufactured in the form of an oligonucleotide probe, a single strand DNA probe, a double strand DNA probe, an RNA probe, or the like. Selection of an appropriate probe and conditions for hybridization can be appropriately selected according to techniques known in the art.

The 'primer' is a nucleic acid sequence having a short free 3' hydroxyl group, which can form a base pair with a complementary template, and is a short nucleic acid sequence that serves as a starting point for template strand copying. Primers can initiate DNA synthesis in the presence of a reagent for polymerization (i.e., DNA polymerase or reverse transcriptase) and four different nucleoside triphosphates at an appropriate buffer and temperature. PCR conditions, the length of the sense and antisense primers can be appropriately selected according to techniques known in the art.

In addition, the present invention provides a method of providing information for diagnosis of metastatic prostate cancer comprising: (a) separating a circulating tumor cell (CTC) isolated from a biological sample; (b) extracting mRNA from the separated circulating tumor cells (CTC); (c) measuring mRNA level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) by using the extracted mRNA as a template: and (d) classifying as prostate cancer when the mRNA level of the genes is increased compared to that of a normal person.

The circulating tumor cells (CTC) may be separated by separating into an antibody that specifically binds to the circulating tumor cells (CTC) and magnetic beads binding to the antibody, and the antibody that specifically binds to the circulating tumor cell (CTC) may be an anti-Epithelial Cell Adhesion Molecule (anti-EpCAM).

In addition, the present invention provides a biomarker composition for predicting prognosis of metastasis potential to prostate cancer comprising a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

In addition, the present invention provides a kit for predicting prognosis of metastasis potential to prostate cancer comprising an agent capable of detecting gene expression level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) as an active ingredient.

In addition, the present invention provides a method of providing information for predicting prognosis of metastasis potential to prostate cancer comprising: (a) separating a circulating tumor cell (CTC) isolated from a biological sample; (b) extracting mRNA from the separated circulating tumor cells (CTC); (c) measuring mRNA level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) by using the extracted mRNA as a template; and (d) classifying as prostate cancer when the mRNA level of the genes is increased compared to that of a normal person.

The circulating tumor cells (CTC) may be separated by separating into an antibody that specifically binds to the circulating tumor cells (CTC) and magnetic beads binding to the antibody, and the antibody that specifically binds to the circulating tumor cell (CTC) may be an anti-Epithelial Cell Adhesion Molecule (anti-EpCAM).

Specifically, the step of separating a circulating tumor cell (CTC) may be performed by injecting a biological sample separated from the subject into one device and sequentially reacting antibodies that specifically bind to circulating tumor cells (CTC) and magnetic beads to separate circulating tumor cells (CTCs), and the device may be a disposable device, but it is not limited thereto.

The biological sample isolated from the subject specifically includes a cell line, histological slide, biopsy, formalin fixed paraffin embedded (FFPE) tissue, body fluid, feces, urine, plasma, serum, whole blood, isolated blood cells, or blood, which are isolated from the subject, and more specifically, blood, but it is not limited thereto.

In addition, the present invention provides a method of screening an agent for preventing or treating metastatic prostate cancer comprising: a first step of selecting a disease subject by measuring expression level of a gene combination comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) in a biological sample isolated from tissue of the subject; and a second step of judging as a formulation for preventing or treating metastatic prostate cancer if the expression level of the gene combination after treatment with a test substance decreases compared to a disease subject not treated with the test substance.

MODE FOR INVENTION

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

<Experimental Example> Experimental Materials and Methods

The following experimental examples are intended to provide experimental examples commonly applied to each of the examples according to the present invention.
1. Experimental Design
In order to confirm whether the gene combination according to the present invention is a biomarker for diagnosis and prognosis prediction of prostate cancer, an experiment was designed in the following three steps.
  (1) Step of removing red blood cells (RBC) from the sample blood using density gradient centrifugation, and targeting circulating tumor cells (CTC) with an anti-EpCAM (epithelial cell adhesion molecule) antibody, and combining the nanoparticle-sized magnetic beads with the anti-epithelial cell adhesion molecule (EpCAM) antibody;
  (2) Step of separating circulating tumor cells (CTC) using a disposable microfluidic device; and
  (3) Step of aligning circulating tumor cells (CTC) by immunostaining method and detecting cancer-related genes using droplet digital polymerase chain reaction (ddPCR).
2. Patient
Between March 2018 and May 2019 (for 14 months), peripheral blood samples of 62 were obtained from five healthy donors and 56 patients who had localized prostate cancer (25 patients), mHSPC stage (metastatic castration-resistant prostate cancer, 9 patients), and mCRPC stage (metastatic hormone-sensitive prostate cancer, 28 patients). All samples were approved by the institutional review committee from Haeundae-Paik Hospital (HPIRB 2018-01-005-004) and Busan-Paik Hospital (180142), and characteristics and clinical information are shown in Table 1 below.

TABLE 1

| | Prostate cancer sample (N* = 56, n† = 62) | | | | |
|---|---|---|---|---|---|
| | Localized stage | | | Metastatic stage | |
| | T2 (N = 11, n = 11) | T3 (N = 8, n = 8) | T4 (N = 6, n = 6) | mHSPC (N = 8, n = 9) | mCRPC (N = 23, n = 28) |
| Age(range) | 70 (55-84) | 71 (62-76) | 75 (59-80) | 75 (64-80) | 75 (57-84) |
| PSA (range) Unit: ng/mL | 4.28 (0.01-22.8) | 13.50 (0.01-83.9) | 1.13 (0.08-3.59) | 80.07 (0.01-678) | 143.62 (0.04-1921) |

TABLE 1-continued

| | Prostate cancer sample (N* = 56, n† = 62) | | | | |
| --- | --- | --- | --- | --- | --- |
| | Localized stage | | | Metastatic stage | |
| | T2 (N = 11, n = 11) | T3 (N = 8, n = 8) | T4 (N = 6, n = 6) | mHSPC (N = 8, n = 9) | mCRPC (N = 23, n = 28) |
| Gleason score | | | | | |
| 6 | 7 (63.63%) | — | — | — | — |
| 7 | 2 (18.18%) | 3 (37.50%) | 1 (16.67%) | — | 1 (43.5%) |
| 8 | 2 (18.18%) | 1 (12.50%) | 2 (33.33%) | 5 (55.56%) | 5 (21.74%) |
| 9 | — | 3 (37.50%) | 3 (50%) | 1 (11.11%) | 10 (43.48%) |
| 10 | — | — | — | 1 (11.11%) | 4 (17.39%) |
| Unknown | — | 1 (12.50%) | — | 2 (22.22%) | 3 (13.04%) |
| Metastatic state | | | | | |
| None | 11 (100%) | 7 (87.50%) | 2 (33.33%) | — | 1 (4.65%) |
| bladder | — | 1 (12.50%) | 4 (66.67%) | — | — |
| Bladder + bone | — | — | — | 8 (100%) | 18 (78.26%) |
| Bladder + lymph node | — | — | — | — | 1 (4.35%) |
| Bladder + bones + other organs | — | — | — | — | 2 (8.70%) |
| Neuroendocrine differentiation | — | — | — | — | 1 (4.35%) |
| Last therapy | | | | | |
| None | 11 (100%) | 8 (100%) | 6 (100%) | 2 (22.22%) | — |
| Radiation therapy | — | — | — | 1 (11.11%) | — |
| Taxane therapy | | | | | |
| Docetaxel | — | — | — | — | 5 (17.86%) |
| Cabazitaxel | — | — | — | — | — |
| Estramustine phosphate | — | — | — | — | 1 (3.57%) |
| Hormone therapy | | | | | |
| GnRH | — | — | — | 6 (66.67%) | 4 (14.29%) |
| HTx | — | — | — | — | 11 (39.29%) |
| Abiraterone | — | — | — | — | 2 (7.14%) |
| Enzalutamide | — | — | — | — | 5 (17.86%) |

N* = Number of patients recruited
n† = Number of patient samples collected

3. Sample Preparation

Peripheral blood samples obtained from patients and healthy donors were stored in Vacutainer tubes (10 ml volume, 367525, Vacutainer®) at 4° C. with the addition of the anticoaguant EDTA (K2E, 18.0 mg), and were tested within 12 hours after collection. Blood samples were first treated with 1.119 g ml Ficoll solution (Histopaque-1119, Sigma-Aldrich), and then subjected to density gradient centrifugation at 700×g for 30 minutes to remove red blood cells (RBC). It was transferred to a 50 mL conical tube and 10 ml ice-cold PBS containing 0.2% BSA was added and washed for 10 minutes at 200×g. After transferring to a 1.5 ml microcentrifuge tube, it was washed with 1 ml ice-cold PBS containing 0.2% BSA, and resuspended in 1 ml ice-cold PBS containing 200 μl 0.2% BSA. According to the instructions of the re-investigation (STEMCELL Technologies), it was reacted on ice with an anti-epithelial cell adhesion molecule (EpCAM) antibody for 60 minutes, and then reacted with nanoparticle-sized magnetic beads for 90 minutes. Then, the sample was diluted with 800 μl (4 times volume) of ice-cold PBS containing 0.2% BSA. For the assay, prostate cancer cell line LNCaP cells (clone FGC, ATCC® CRL-1740™) were stained with a membrane-permeable green fluorescent nucleic acid dye (SYTO 13, Invitrogen), and blood nuclear cells were stained with red fluorescent nucleic acid dye (SYTO). 64, Invitrogne).

4. Device Fabrication and Setting

A disposable microfluidic device was used to separate circulating tumor cells (OTCs) from the sample. The device was set by firstly placing a reusable substrate on two stacked neodymium-iron-boron (Nd—Fe—B) permanent magnets, and attaching disposable microfluidic superstraight using a vacuum air injection system so that the reused substrate was aligned at −50 kPa pressure.

5. Isolation of Circulating Tumor Cells (CTC)

The assembled disposable CTC-μChip consists of a disposable superstraight and reusable functional substrate. The disposable superstraight has two inlets, two outlets and a vacuum trench surrounding the microchannel. The reusable substrate contains magnetic wires that create a strong magnetic field in the microchannels, a key function of the CTC isolation mechanism. Disposable superstraits and reusable substrates can be simply assembled and disassembled using vacuum application programs.

After assembling the device, a blood sample and phosphate-buffered saline (PBS) containing 0.2% BSA (bovine serum albumin) were injected into each of the two inlets (a sample in the inlet #1, and a PBS solution in the inlet #2). When a uniform external magnetic field is applied to the ferromagnetic line, a high-density magnetic field is created through the entire area of the microchannel. Subsequently, the CTC is separated along the inclined ferromagnetic wire according to the CTC outlet (exit #2), and the remaining unbound cell nucleus is separated into the waste outlet (exit #1). Eventually, the OTCs bound to the immunomagnetic nanobeads are arranged laterally, discharged through the outlet for genomic analysis, and the remaining normal cell nuclei are discharged through the waste outlet.

6. Immunostaining and Detection

CTC was counted through image analysis. The isolated CTC was fixed with 100 μl of 4% paraformaldehyde, and stained with a membrane-permeable nucleic acid fluorescent dye (DAPI, Invitrogen) and an anti-CD45-Alexa 647 (Biolegend) antibody for 30 minutes. Then 100 μl of 0.2% Triton X-100 (AMRESCO) was treated for 10 minutes, and anti-pan-cytokeratin-Alexa 488 (eBioscience) antibody was treated for 30 minutes. In order to count CTC and normal blood cells, fluorescently stained samples were observed with a confocal microscope (LSM800; Carl Zeiss).

The stained area and morphological characteristics such as nuclear size and cytoplasmic area of CTC was confirmed. If anti-pan-cytokeratin staining was present, and the round shape had a larger nucleus than white blood cells, it was selected as CTC. Pan-cytokeratin-positive cells were considered as CTC, even if the nucleus size was the same as or smaller than that of normal cells. In addition, in the case of green fluorescence staining, a nucleus having a size of ≥9 μm and a cell diameter of ≥15 μm, it was considered as CTC. The cases with CD45 red fluorescent lobes and multiple nuclei were considered as leukocytes. Even if they were not stained with CD45, the nucleus morphology and cell size were determined. In particular, double positive staining cells were regarded as leukocytes.

Example 1: Target Gene Selection

The presence of CTC was confirmed and patient samples were collected to confirm the mRNA-based gene expression level of the cancer-specific gene, and each cancer patient was classified according to the clinical cancer stage to compare gene expression diversity. After CTC separation, mRNA was extracted and cDNA was synthesized.

After CTC separation, cells were lysed in 300 μl of lysis/binding buffer (Dynabeads mRNA Direct Kit; Invitrogen). To the sample, magnetic beads having diameter of 2.8 μm (Dynabeads Oligo(dT)25; Invitrogen) were added at a concentration of 20 μl and mixed for 10 minutes to specifically bind to the poly-A tail of mRNA. Thereafter, the sample was placed on a magnet for 2 minutes to collect mRNA-bound oligo-dT beads. After washing with a buffer solution, 10 μl of an elution buffer (10 mM Tris-HCL pH 7.5) was added according to the manufacturer's protocol and reacted at 75° C. for 2 minutes to isolate mRNA. The isolated mRNA was synthesized with Accu Power CycleScript RT PreMix (dT20) (Bioneer) in which 10 μl of 0.1% diethylpyrocarbonate (DEPC) was dissolved. After adding the mRNA to the RT premix solution, the reaction mixture was incubated in a heat cycle at 42° C. for 90 minutes, and terminated with an RNase inactivation step at 95° C. for 5 minutes.

The mRNA-based cancer-related target gene was designed for genomic analysis of gene expression levels in prostate cancer patients. AR and AR-V7 related to androgen hormone were selected to validate male and variant. EpCAM and KRT-19, which are epithelial cell-specific genes, were selected to confirm the presence of CTC in the isolated samples. Prostate specific genes PSA and PSMA were selected to identify patients with prostate cancer.

Example 2: Pre-amplification

To evaluate each gene, endpoint PCR and multiplex PCR were used. A pre-amplification primer set was designed to analyze selected AR, AR-V7, EpCAM, KRT-19, PSA and PSMA genes to identify prostate cancer patients. The primer sets used for pre-amplification are shown in Table 2 below.

TABLE 2

| Genes | Size (bp) | | Base sequence (5'-3') | SEQ. ID NO. |
|---|---|---|---|---|
| AR | 390 | F | TCTCTCAAGAGTTTGGATGGC | 1 |
| | | R | ACTGGGTGTGGAAATAGATGG | 2 |
| AR-V7 | 440 | F | GTGCGCCAGCAGAAATGA | 3 |
| | | R | ATGCCAAGCCACATTACAGG | 4 |
| EpCAM | 755 | F | CTCGCGTTCGGGCTTC | 5 |
| | | R | TCAGGTGCTTTTTCATCAACATTA | 6 |
| KRT-19 | 695 | F | CGACTACAGCCACTACTACAC | 7 |
| | | R | CACTATCAGCTCGCACATCG | 8 |
| PSA | 435 | F | GGTGATGACTCCAGCCAC | 9 |
| | | R | CACGATGGTGTCCTTGATCC | 10 |
| PSMA | 643 | F | AGCATTTTTGGATGAATTGAAAGC | 11 |
| | | R | TGGTAACCTGGTGTGAGA | 12 |
| β-actin | 791 | F | GGCACCAGGGCGTGA | 13 |
| | | R | GCCGCCAGACAGCAC | 14 |
| GAPD | 605 | F | AGAACGGGAAGCTTGTCATC | 15 |
| | | R | CTGCTTCACCACCTTCTTGA | 16 |
| PTPRC (CD45) | 544 | F | TGTTGTAAAGATAACCAGCAC | 17 |
| | | R | CTGTGTCCTCCAGCTCCTA | 18 |

CDNA was synthesized in 2000 LNCaP cells. Leukocyte cells separated together were measured using a specific marker gene PTPRC (CD-45). Two templates and a single PCR master mix (AccuPower HotStart PCR PreMix; Bioneer) were mixed with each gene primer set (10 pmol/μl) at the same ratio to prepare a final 100 nM, and the genes were evaluated according to the manufacturer's protocol. In the case of multiplex PCR, after adding the same amount of primer sets to the multiplex PCR premix (AccuPower Multiplex PCR PreMix; Bioneer) and cDNA template, the genes were evaluated according to the manufacturer's protocol (FIG. 1).

As shown in FIG. 1, in the negative control (NC) with only white blood cells (WBC), only the bands of the housekeeping genes (GAPDH, β-actin) and PTPRC genes appeared, but in the sample mixed with LNCaP cells, the bands of AR, AR-V7, EpCAM, KRT-19, PSA and PSMA genes were shown.

Example 3: Target Gene Evaluation Using ddPCR

In order to evaluate target gene primers specific for each gene, the original template and the serially diluted pre-amplification template were measured using the ddPCR method. The primer sets used are shown in Table 3 below.

TABLE 3

| Genes | Size (bp) | | Base sequence (5'-3') | SEQ. ID NO. |
|---|---|---|---|---|
| AR | 125 | F | CAGCCTATTGCGAGAGAGCTG | 19 |
|  |  | R | GAAAGGATCTTGGGCACTTGC | 20 |
| AR-V7 | 125 | F | CCATCTTGTCGTCTTCGGAAATGTTA | 21 |
|  |  | R | TTTGAATGAGGCAAGTCAGCCTTTCT | 22 |
| EpCAM | 287 | F | GTTCGGGCTTCTGCTTGC | 23 |
|  |  | R | GCTCTCATCGCAGTCAGGA | 24 |
| KRT-19 | 211 | F | TTTGAGACGGAACAGGCTCT | 25 |
|  |  | R | AATCCACCTCCACACTGACC | 26 |
| PSA | 161 | F | ACCAGAGGAGTTCTTGACCCCAAA | 27 |
|  |  | R | CCCCAGAATCACCCGAGCAG | 28 |
| PSMA | 188 | F | ATGAATTGAAAGCTGAGAACATCAAGA | 29 |
|  |  | R | GGGATGAGTCTTATTTGGGTAGGAC | 30 |
| β-actin | 791 | F | GTACCACTGGCATCGTGATGGA | 31 |
|  |  | R | GCCATCTCTTGCTCGAAGTCCAG | 32 |
| GAPD | 144 | F | TGCACCACCAACTGCTTAGC | 33 |
|  |  | R | GGCATGGACTGTGGTCATGAG | 34 |
| PTPRC (CD45) | 117 | F | CTTCAGTGGTCCCATTGTGGTG | 35 |
|  |  | R | CCACTTTGTTCTCGGCTTCCAG | 36 |

The cDNA template of 2000 LNCaP cells was multiplexed pre-amplified in 18 cycles. β-actin and GAPDH genes were used as housekeeping genes, PTPRC gene was used for selection of negative control (white blood cells), and six genes (AR, AR-V7, EpCAM, KRT-19, PSA, PSMA) were used to evaluate the sample. The pre-amplified samples serially diluted 10 times were amplified with a PCR super mix (QX200 ddPCR EvaGreen Supermix, BioRad) together with the target gene primer set in Table 3 above. To create a droplet, all PCR mixtures were loaded in a droplet generation cartridge (DG8™ cartridges for QX100™/QX200™ droplet generator, Bio-Rad) with 70 µl of droplet generation oil (Droplet Generation Oil for EvaGreen, Bio-Rad) and reacted with a droplet generator (QX200, Droplet Generator, Bio-Rad). The droplets generated before PCR were transferred to a 96 well PCR plate and sealed using a thermal sealer (PX1™ PCR Plate Sealer, Bio-Rad) to prevent evaporation. After reacting the sealed PCR plate with a PCR machine (GeneAmp® PCR System 9700, Applied Biosystems), the result was confirmed with a droplet reader (QX200™, Droplet Reader, Bio-Rad) (FIG. 2).

All genes showed well-separated positive and negative signals, and the cut-off threshold amplitude was analyzed according to the fine separation point. The threshold value was different depending on the primer quality and the specificity for the target gene sequence. The threshold for the AR gene is 14500, the threshold for the AR-V7 gene is 15345, the threshold for the EpCAM gene is 16000-19000, the threshold for the KRT-19 gene is 11000-14000, the threshold for the PSA gene is 14000-18000, and the threshold for the PSMA gene is 16000-19000. The original copy number concentration was 74.3 µl in AR, 0.62 µl in AR-V7, 87.3 µl in EpCAM, 19.2 µl in KRT-19, 1128 µl in PSA, 284 µl in PSMA, and 1657 µl in GAPDH. The pre-amplified copy number exceeded the original copy number, and was found to be saturated in 1/100 dilution samples in PSA, PSMA, and GAPDH in which the original copy number exceeded 100. All of the 1/1000 diluted samples were found to decrease linearly. The number of copies of the threshold is 0.13 copies/µl for AR, 0.28 copies/µl for AR-V7, 0.17 copies/µl for EpCAM, 0.11 copies/µl for KRT-19, 0.01 copies/µl for PSA, 0.23 copies/µl for PSMA.

Example 4: Evaluation of Patient Sample Concentration

Samples of prostate cancer patients at localized stage (N=2), mHSPC stage (N=2), and mCRPC stage (N=3) were used for template concentration evaluation. When using the pre-amplified template, all signals due to the high concentration were measured positively. In order to optimize the template concentration, the pre-amplified cDNA template was diluted by ½, ⅕, 1/10, and 2.5 p µl of each gene was used, and the primer set of the target gene shown in Table 3 above (5 pmole/µl of forward primer and 5 pmole/µl of reverse primer) were added to a supermix (QX200 ddPCR EvaGreen Supermix, Bio-Rad), followed by ddPCR.

As a result of measuring the amplitude cutoff value, it was found that the AR gene decreased in proportion to the dilution factor to 14206-17000, and the AR-V7 gene was found to be 17645 at high concentration, and the EpCAM gene was 16008-16662, and all samples showed positive signals and decreased linearly with the dilution factor, and the KRT-19 gene was found to decrease linearly according to the concentration in only mCRPC patients from 11751 to 15898, and the PSA gene was found to decrease linearly according to the concentration only in mCRPC patients from 14370 to 16553, and the PSMA gene was found to decrease linearly according to the concentration from 16062 to 17427. The threshold of the detected amplitude cutoff value was applied to all patient samples.

Example 5: CTC Model Analysis Evaluation

In order to verify the method of diagnosing and predicting prognosis of prostate cancer according to the present invention, the performance of the disposable microfluidic device and the optimized separation condition were evaluated. As a cancer patient model, approximately 100 of LNCaP cell lines was inoculated into 5 mL of healthy blood. A disposable microfluidic device was prepared on a stack of two neodymium permanent magnets generating an external magnetic flux of 0.2 T and applied in the horizontal direction of the microfluidic channel. During separation, LNCaP cells were separated by the CTC outlet and counted using a fluorescence microscope for evaluating the recovery rate. The collected samples were counted for LNCaP cells and white blood cells (WBCs) isolated together under a fluorescence microscope to measure the purity and consumption rate. Various samples were evaluated by repeating 3 times with 1, 2 and 4 ml/h flow rates to determine the optimal flow rate for the sample.

According to the analytical evaluation, the recovery rate was 95.13±1.20% at 1 ml/h, 93.6±0.79% at 2 ml/h, and 84±7.00% at 4 ml/h, showing an average of 90.91%. Because the white blood cells that died during sample preparation non-specifically bind to the immunomagnetic beads and aggregate, the white blood cells were co-separated from the CTC, and the number of white blood cells per 5 ml blood sample was shown to be 238-786 cell range. The average number of leukocytes contaminated was 660 cells/5 ml at 1 ml/h, 667 cells/5 ml at 2 ml/h, and 374.33 cells/5 ml at 4 ml/h, and the average of leukocytes was 567.11 cells/5 ml (113.42 cells/ml). That is, the average leukocyte depletion rate is measured as 44083.16-fold (4.64 log), assuming that 5×10⁶ leukocyte cells per ml of blood are present. As the flow rate increased, the number of co-separated leukocytes decreased, with 13.09% at 1 ml/h, 13.93% at 2 ml/h, and 19.77% at 4 ml/h and an average of 15.60%.

Since the CTC attraction force generated by the high gradient magnetic flux in the microchannel is lower than the dynamic drag force of the fluid, the recovery rate decreased as the flow rate increased. At a flow rate of 4 ml/h, the recovery rate slightly decreased, but the number of leukocytes decreased significantly and the purity was increased. At a flow rate of 1 ml/h, the recovery rate was the highest, but the purity was low due to long treatment. Overall, a 2 ml/h flow rate at which a recovery rate is 93.60%, a reasonable purity is 13.93% and a leukocyte depletion rate is 4.57 log was suitable as an optimized sample flow rate.

Example 6: CTC Detection 3-5 mL of peripheral blood was collected from patients in the localized stage of cancer (n=25) and metastatic stage (n=37) and from healthy donors (n=5). Recruited samples in the metastatic stage were repeated 1 for mHSPC (metastatic hormone-sensitive prostate cancer) and repeated 5 for mCRPC (metastatic castration-resistant prostate cancer). Samples and buffers were added at a flow rate of 2 ml/h, which is an optimized condition for the process. After separating the CTC, the collected samples were subjected to immunostaining. Thereafter, fluorescence and morphological specificity were analyzed to distinguish OTCs and leukocytes (FIG. 4). In order to quantify the separated CTC and remaining cells, the number of each cells listed was divided by the volume of the separated blood, and finally counted into a volume of 1 mL and analyzed.

As shown in FIG. 5, the average number of OTCs and white blood cells in healthy donors (HD) was 0.94 CTCs/mL and 602.23 WBCs/mL. The average number of OTCs and leukocytes isolated in the localized stage was 6.58 CTCs/mL and 514.41 WBCs/mL. In the metastatic stage, the average number of OTCs and leukocytes was 16.77 CTCs/mL and 717.64 WBCs/mL in the mHSPC stage, and 31.02 CTCs/mL and 627.62 WBCs/mL in the mCRPC stage. That is, the average number of OTCs in the metastatic stage was 27.55 CTCs/mL, which was 4.17 times higher than in the localized stage. In addition, it was shown that the level of PSA protein in the blood increased as the degree of cancer progression became malignant.

Purity rate is calculated in the process of separating CTC and leukocytes, and is defined as the ratio of cytokeratin positive cells versus CD45 positive cells. As shown in FIG. 5, the purity rate was 0.17% in healthy donors (HD), 2.09% in the localized stage, 3.79% in mHSPC, and 6.71% in the mCRPC stage. As for the purity rate, as the cancer progression worsens, the number of CTCs increases, so the purity rate also increases.

In addition, the blood of the patient compared to the blood of a healthy donor is viscous and the number of white blood cells isolated was 5.25 times higher and the purity rate was 3.53 times lower.

Example 7: Cancer-related Gene Analysis

Samples of all patients were analyzed using ddPCR to detect cancer-related genes in mRNA. The gene detection rate was analyzed by the percentage of genes detected in each step, and the gene expression level was measured by the copy number concentration.

TABLE 4

|  |  | AR | AR-V7 | EpCAM | KRT-19 | PSA | PSMA |
|---|---|---|---|---|---|---|---|
| Normal donor (n = 5) | Detection rate (%) | 40 | 0 | 60 | 40 | 0 | 0 |
|  | Concentration (copy/μl) | 18.55 (3.80-33.3) | — | 14.10 (9.60-21.50) | 73.80 (22.6-125) | — | — |
| Localized stage (n = 25) | Detection rate (%) | 76 | 0 | 96 | 40 | 40 | 36 |
|  | Concentration (copy/μl) | 274.94 (0.43-1140) | — | 7.54 (0.21-57.10) | 2.83 (0.14-25.90) | 0.19 (0.07-0.67) | 6.93 (0.27-33.70) |
| mHSPC stage (n = 9) | Detection rate (%) | 88.89 | 11.11 | 88.89 | 66.67 | 55.56 | 55.56 |
|  | Concentration (copy/μl) | 395.88 (6.20-928) | 11.10 | 32.80 (0.41-181) | 9.04 (0.23-35.70) | 38.47 (0.07-131) | 19.56 (0.29-38.9) |
| mCRPC stage (n = 28) | Detection rate (%) | 100 | 28.57 | 100 | 82.14 | 89.29 | 82.14 |
|  | Concentration (copy/μl) | 845.23 (0.44-5440) | 79.86 (0.37-434) | 534.74 (0.43-7160) | 579.79 (0.20-5250) | 1575 (0.08-7240) | 1006.95 (0.3-8900) |

As shown in Table 4, the detection rate of AR, a gene related to androgen hormone therapy, was 40% in healthy donors (HD), 76% in localized stage, 76% in mHSPC stage, and 100% in mCRPC stage. The expression level of AR increased as the cancer progression became malignant. The detection rate of AR-V7 (Androgen receptor variant 7) was 11.1% in the mHSPC stage and 28.57% in the mCRPC stage, and the expression level was 7.19 times higher in the mCRPC stage than in the mHSPC stage.

The detection rate of EpCAM (Epithelial cell adhesion molecule) was high in all patients, and the detection rate of KRT-19 (Cytokeratin 19) was high in mHSPC and mCRPC stages. Both the PSA gene and the PSMA gene were detected in cancer patients, and the expression level of the gene increased as the malignancy of cancer progressed.

That is, as for AR (Androgen receptor), AR-V7 (Androgen receptor variant 7, androgen receptor variant 7), EpCAM (Epithelial cell adhesion molecule), KRT-19 (Cytokeratin 19, cytokeratin 19), PSA (Prostate specific antigen) and PSMA (Prostate specific membrane antigen) genes, it was found that the detection rate increased and the expression level increased as the cancer progression stage progressed to the localized stage, mHSPC stage, and mCRPC stage.

The above results demonstrate that the AR (Androgen receptor), AR-V7 (Androgen receptor variant 7), EpCAM (Epithelial cell adhesion molecule), KRT-19 (Cytokeratin 19).), PSA (Prostate specific antigen) and PSMA (Prostate specific membrane antigen) gene combination can not only be used as a genetic marker for diagnosing prostate cancer, but also can be used as a marker capable of diagnosing or predicting the prognosis of malignancy of cancer by measuring the detection rate and expression level.

Example 8: PSA Level in Blood

PSA protein in blood is used as a diagnostic and prognostic marker for prostate cancer in the blood circulation system. In the early stages of prostate cancer, the PSA protein is highly expressed in the localized prostate tumor stage, and it has been known as an indicator of the patient's prognosis in the entire cancer stage.

As shown in FIG. 8, the PSA gene concentration of CTC and the clinical blood PSA concentration in the patient were shown as a linear plot at the low serum level of the patient. At the localized stage, PSA concentrations and gene levels were lower than the risk level. In the mHSPC stage and the mCRPC stage, the PSA level in the blood increased according to the risk and was found to be related.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of diagnosing and treating metastatic prostate cancer comprising:

(a) separating circulating tumor cells (CTCs) isolated from a biological sample at a flow rate of 2 ml/h using a disposable microfluidic device;

(b) extracting mRNA from the separated circulating tumor cells (CTCs);

(c) measuring mRNA level of genes comprising AR (Androgen receptor), AR-V7 (Androgen receptor variant 7), EpCAM (Epithelial cell adhesion molecule), KRT-19 (Cytokeratin 19), PSA (Prostate specific antigen) and PSMA (Prostate specific membrane antigen) by droplet digital PCR using the extracted mRNA as a template:

(d) classifying as metastatic castration-resistant prostate cancer (mCRPC) when the mRNA levels of all of the genes are increased compared to that of a healthy person; and (e) administering a taxane therapy selected from the group consisting of docetaxel, cabazitaxel, and estramustine phosphate to a subject classified as having the mCRPC in step (d).

2. The method of claim 1, wherein the circulating tumor cells (CTCs) are separated using an antibody specifically binding to the circulating tumor cells (CTCs) and magnetic beads binding to the antibody.

3. The method of claim 2, wherein the antibody specifically binding to the circulating tumor cells (CTCs) is an anti-EpCAM antibody (anti-Epithelial Cell Adhesion Molecule antibody).

* * * * *